United States Patent
Ma et al.

(10) Patent No.: US 7,968,489 B2
(45) Date of Patent: *Jun. 28, 2011

(54) METHODS OF PREPARING SUPPORTED CATALYSTS FROM METAL LOADED CARBON NANOTUBES

(75) Inventors: Jun Ma, Lexington, MA (US); David Moy, Germantown, MD (US); Asif Chishti, Lowell, MA (US); Jun Yang, Bedford, MA (US)

(73) Assignee: Hyperion Catalysis International, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/841,359

(22) Filed: Aug. 20, 2007

(65) Prior Publication Data

US 2008/0039315 A1   Feb. 14, 2008

Related U.S. Application Data

(63) Continuation of application No. 11/281,814, filed on Nov. 16, 2005, now abandoned.

(60) Provisional application No. 60/628,469, filed on Nov. 16, 2004.

(51) Int. Cl.
| | |
|---|---|
| B01J 21/18 | (2006.01) |
| B01J 27/06 | (2006.01) |
| B01J 23/00 | (2006.01) |
| B01J 23/02 | (2006.01) |
| B01J 23/06 | (2006.01) |
| B01J 23/40 | (2006.01) |
| B01J 23/74 | (2006.01) |

(52) U.S. Cl. ........ 502/185; 502/180; 502/181; 502/182; 502/183; 502/184; 977/742; 977/745; 977/748; 977/750; 977/752

(58) Field of Classification Search .......... 502/180–185; 977/742, 745, 748, 750, 752
See application file for complete search history.

(56) References Cited

U.S. PATENT DOCUMENTS

| | | |
|---|---|---|
| 4,663,230 A | 5/1987 | Tennent |
| 5,165,909 A | 11/1992 | Tennent et al. |
| 5,171,560 A | 12/1992 | Tennent |
| 5,424,054 A | 6/1995 | Bethune et al. |
| 5,456,897 A | 10/1995 | Moy et al. |
| 5,500,200 A | 3/1996 | Mandeville et al. |
| 5,569,635 A | 10/1996 | Moy et al. |
| 5,691,054 A | 11/1997 | Tennent et al. |

(Continued)

FOREIGN PATENT DOCUMENTS

JP    2002-110178    *  4/2002

(Continued)

OTHER PUBLICATIONS

Search Report for PCT/US05/41603.*

(Continued)

*Primary Examiner* — Patricia L Hailey

(57) ABSTRACT

A new method for preparing a supported catalyst is herein provided. Carbon nanotubes are functionalized by contacting them with an oxidizing agent to form functionalized carbon nanotubes. A metal catalyst is then loaded or deposited onto the functionalized carbon nanotubes. The mixture is then extruded to form the supported catalyst comprising a carbon nanotube structure containing metal catalyst more evenly dispersed within the internal structure of the carbon nanotube structure.

20 Claims, 4 Drawing Sheets

U.S. PATENT DOCUMENTS

| | | | |
|---|---|---|---|
| 5,707,916 | A | 1/1998 | Snyder et al. |
| 5,965,470 | A | 10/1999 | Bening et al. |
| 6,031,711 | A | 2/2000 | Tennent et al. |
| 6,099,965 | A | 8/2000 | Tennent et al. |
| 6,143,689 | A | 11/2000 | Moy et al. |
| 6,203,814 | B1 | 3/2001 | Fisher et al. |
| 6,333,016 | B1 | 12/2001 | Resasco et al. |
| 6,432,866 | B1 * | 8/2002 | Tennent et al. ............ 502/180 |
| 6,761,870 | B1 | 7/2004 | Smalley et al. |
| 6,824,689 | B2 * | 11/2004 | Wang et al. ............... 210/660 |
| 6,827,919 | B1 | 12/2004 | Moy et al. |
| 7,081,429 | B2 * | 7/2006 | Kishi et al. ............... 502/182 |
| 7,122,165 | B2 * | 10/2006 | Wong et al. ............... 423/447.2 |
| 7,179,561 | B2 * | 2/2007 | Niu et al. .................. 429/44 |
| 7,345,005 | B2 * | 3/2008 | Kourtakis .................. 502/182 |
| 2002/0049134 | A1 * | 4/2002 | Imazato ..................... 502/101 |
| 2002/0121460 | A1 * | 9/2002 | Moy et al. ................. 208/133 |
| 2003/0042147 | A1 | 3/2003 | Talin et al. |
| 2003/0180526 | A1 | 9/2003 | Winey et al. |
| 2003/0181328 | A1 | 9/2003 | Hwang et al. |
| 2006/0137817 | A1 * | 6/2006 | Ma et al. ................... 156/296 |
| 2006/0142148 | A1 * | 6/2006 | Ma et al. ................... 502/185 |
| 2006/0142149 | A1 * | 6/2006 | Ma et al. ................... 502/185 |
| 2008/0031802 | A1 | 2/2008 | Ma et al. |
| 2008/0176052 | A1 * | 7/2008 | Ma et al. ................... 428/219 |
| 2009/0093360 | A1 * | 4/2009 | Ma et al. ................... 502/182 |
| 2010/0086471 | A1 * | 4/2010 | Ma et al. ................... 423/447.2 |

FOREIGN PATENT DOCUMENTS

| | | |
|---|---|---|
| WO | 8907163 A1 | 8/1989 |
| WO | 9105089 A1 | 4/1991 |
| WO | 9507316 A1 | 3/1995 |
| WO | 9732571 A1 | 9/1997 |
| WO | 0107694 A1 | 2/2001 |
| WO | 02095098 A1 | 11/2002 |
| WO | WO 02/095098 | 11/2002 |
| WO | 2006135439 A2 | 12/2006 |

OTHER PUBLICATIONS

"Graphitic cones in palladium catalysed carbon nanofibres," H. Terrones et al. Chemical Physics Letters 343 (2001), pp. 241-250.*

International Search Report, PCT/US05/41603, Aug. 28, 2006.
Supplementary European Search Report, EP 05 85 1732, Jul. 22, 2009.
Baker and Harris, Chemistry and Physics of Carbon, Walker and Thrower ed., vol. 14, 1978, p. 83.
Bethune, D S, et al., "Cobalt-catalysed Growth of Carbon Nanotubes With Single-Atomic-Layer Walls," Nature, vol. 363, p. 605-607 (1993).
Dai, H., et al., "Single-Wall Nanotubes Produced by Metal-Catalyzed Disproportionation of Carbon Monoxide," Chemical Physics Letters 260: 471-475 (1996).
de Heer, Walt A., "Nanotubes and the Pursuit of Applications," MRS Bulletin, Apr. 2004.
Georgakilas, V., et al., "Organic Functionalization of Carbon Nanotubes," JACS Communications, 124, pp. 760-761 (2002).
Guo, T., et al., "Catalytic growth of single-walled nanotubes by laser vaporization," Chem. Phys. Lett., vol. 243: Issues 1-2, pp. 49-54 (1995).
Hirsch and Vostrowsky, "Functionalization of Carbon Nanotubes," Topics in Current Chemistry, 245:193-237 (2005).
Holzinger, M., et al., "[2+1] cycloaddition for cross linking SWCNTs," Carbon 42, pp. 941-947 (2004).
Iijima, S., "Helical microtubules of graphitic carbon," Nature 354:56-58 (1991).
Iijima, S. and Ichihashi,T., "Single-shell carbon nanotubes of 1-nm diameter," Nature, vol. 363, pp. 603-605 (1993).
Kitiyanan, B., "Controlled production of single-wall carbon nanotubes by catalytic decomposition of CO on bimetallic Co-Mo catalysts," Chemical Physics Letters, 317:497-503 (2000).
Oberlin, A. & Endo, M., "Filamentous Growth of Carbon Through Benzene Decomposition," J. of Crystal Growth, vol. 32, pp. 335-349 (1976).
Rodriguez, N., "A Review of Catalytically Grown Carbon Nanofibers," J. Mater. Research, vol. 8, pp. 3233-3250 (1993).
Thess, A., et al., "Crystalline Ropes of Metallic Carbon Nanotubes," Science, 273:483-487 (1996).
Weaver, J.H., "Totally Tubular," Science 265, pp. 611-612 (1994).
Hoch, et al., U.S. Appl. No. 10/875,435, "Functionalized Single Walled Carbon Nanotubes," filed Jun. 23, 2004.

* cited by examiner

US 7,968,489 B2

METHODS OF PREPARING SUPPORTED CATALYSTS FROM METAL LOADED CARBON NANOTUBES

CROSS REFERENCE INFORMATION

This application is a continuation of U.S. Ser. No. 11/281,814, filed Nov. 16, 2005 which claims benefit to and priority of U.S. Provisional Application No. 60/628,469, filed Nov. 16, 2004, each of which is hereby incorporated by reference in their entirety.

FIELD OF THE INVENTION

The invention relates to a new method for preparing supported catalyst by predeposition of the catalyst or catalyst precursor onto the carbon nanotube followed by formation of a carbon nanotube structure with the predeposited or metal loaded carbon nanotube. The result is a supported catalyst comprising a carbon nanotube structure with metal catalysts more evenly and thoroughly dispersed in the structure. As such, the supported catalyst of the present invention contains a higher concentration and better distribution of metal catalysts, leading to more efficient and higher yields of the desired final product.

BACKGROUND OF THE INVENTION

Supported Catalysts

Supported catalysts (i.e., catalysts which are supported on some sort of surface, structure, or support, etc.) typically comprise an inert support material and a catalytically active material. Because heterogeneous reactions are normally carried out at elevated temperatures (and sometimes at elevated pressures as well) and in a reactive atmosphere, the exact chemical nature of the active catalyst component within the reaction zone can be difficult to determine. Thus, the terms "catalyst" or "supported catalyst" are often used interchangeably in the industry to refer to the composition comprising both the inert support and catalytically active material that is charged into the reaction zone, although it is acknowledged that the exact nature of the active material within the reaction zone is usually not determinable.

Supported catalysts may be prepared by, for example, initially depositing precursors of the actual catalytically active material onto the inert support and then treating them accordingly (e.g., calcination), before feeding them into the reaction zone. More extensive pre-treatments and passivation steps to stabilize the supported catalyst before feeding to the reaction zone are also common. In a common example, metal salts are deposited onto inert support, converted into metal oxides by calcinations at elevated temperatures and then further reduced in situ to active pure metal catalysts.

Supported catalysts are widely used in heterogeneous catalytic reactions for chemical processes in the petroleum, petrochemical and chemical industries. Such reactions are commonly performed with the reactant(s) and product(s) in the fluid phase and the catalyst in the solid phase. In heterogeneous catalytic reactions, the reaction occurs at the interface between the phases, i.e., the interface between the fluid phase of the reactant(s) and product(s) and the solid phase of the supported catalyst. Hence, the properties of the surface of a heterogeneous supported catalyst are important factors in the effective use of the catalyst.

For example, the surface area of the active catalyst, as supported, and the accessibility of that surface area to reactant adsorption and product desorption are important. These factors affect the activity of the catalyst, i.e., the rate of conversion of reactants to products.

Generally, catalytic activity is proportional to catalyst surface area. Therefore, a high specific area is desirable. However, the surface area should be accessible to reactants and products as well as to heat flow.

The active catalyst material may be supported on the external and/or internal structure of a support. Often, the internal structure of a support can contain a greater surface area than the external surface, because of the internal porosity. The chemisorption of a reactant by a catalyst surface is preceded by the diffusion of that reactant through the internal structure of the support.

Therefore, when an ample amount of active catalysts are located or supported in the internal structure of a support, the accessibility of the internal structure of the support to reactant(s), product(s) and heat flow is important. Accessibility is measured by porosity and pore size distribution. Activated carbons and charcoals used as catalyst supports may have surface areas of about a thousand square meters per gram, and porosities of greater than 1 ml/gm. However, much of this surface area and porosity (e.g., as much as 50%, and often more), is often associated with micropores (i.e., pores with pore diameters of 2 nm or less). These pores can be inaccessible because of diffusion limitations. They are easily plugged and thereby deactivated. Thus, high porosity materials where the pores are mainly in the mesopore region (i.e., 2-50 nm) or macropore region (i.e., greater than 50 nm) are most desirable.

It is also important that supported catalysts not fracture or attrit during use because such fragments may become entrained in the reaction stream and must then be separated from the reaction mixture. The cost of replacing attritted catalyst, the cost of separating it from the reaction mixture and the risk of contaminating the product are all burdens upon the process. In slurry phase, e.g., where the solid supported catalyst is filtered from the process stream and recycled to the reaction zone, the attritted fines may plug the filters and disrupt the process.

The chemical purity of the catalyst and the catalyst support also have important effects on the selectivity of the catalyst, i.e., the degree to which the catalyst produces one product from among several products, and the life of the catalyst. Thus, it is also important that a catalyst, at the very least, minimize its contribution to the chemical contamination of reactant(s) and product(s). In the case of a catalyst support, this is even more important since the support is a potential source of contamination both to the catalyst it supports and to the chemical process. Further, some catalysts are particularly sensitive to contamination that can either promote unwanted competing reactions, i.e., affect its selectivity, or render the catalyst ineffective, i.e., "poison" it. For example, charcoal and commercial graphites or carbons made from petroleum residues usually contain trace amounts of sulfur or nitrogen. Carbons of natural resources may contain these materials as well as metals common to biological systems and may be undesirable for that reason.

Another important factor which can affect the efficiency of a supported catalyst is the amount of active catalysts in or on the support, as well as the distribution of the active catalysts throughout or within the support itself. Supported catalyst which contain more active catalysts in or on the support will generally have better results and catalytic activity than supported catalyst mainly comprised of the support material with few active catalysts. Furthermore, supported catalysts which have catalytic materials more evenly dispersed throughout or within the support generally have higher yield and catalytic activity than supported catalysts which have poor distribution of the catalytic material in or on the support.

Carbon Nanotubes

Carbon nanotubes have been identified as materials of interest for use as catalysts and catalyst supports. Carbon nanotubes exist in a variety of forms and have been prepared through the catalytic decomposition of various carbon-containing gases at metal surfaces.

Carbon nanotubes (also known as fibrils) are vermicular carbon deposits having diameters less than $1.0\mu$, preferably less than $0.5\mu$, and even more preferably less than $0.2\mu$. Carbon nanotubes can be either multi walled (i.e., have more than one graphene layer more or less parallel the nanotube axis) or single walled (i.e., have only a single graphene layer parallel to the nanotube axis). Other types of carbon nanotubes are also known, such as fishbone fibrils (e.g., wherein the grapheme layers exhibit a herringbone pattern with respect to the tube axis), etc. As produced, carbon nanotubes may be in the form of discrete nanotubes, aggregates of nanotubes (i.e., dense, microscopic particulate structure comprising entangled carbon nanotubes) or a mixture of both.

Processes for forming carbon nanotubes are well known. E.g., Baker and Harris, *Chemistry and Physics of Carbon*, Walker and Thrower ed., Vol. 14, 1978, p. 83; Rodriguez, N., *Journal of Materials Research*, Vol. 8, p. 3233 (1993); Oberlin, A. and Endo, M., *Journal of Crystal Growth*, Vol. 32 (1976), pp. 335-349; U.S. Pat. No. 4,663,230 to Tennent; U.S. Pat. No. 5,171,560 to Tennent; Iijima, Nature vol. 354, 56, 1991; Weaver, Science 265, 1994; de Heer, Walt A., "Nanotubes and the Pursuit of Applications," *MRS Bulletin*, April, 2004; etc; "Single-shell carbon nanotubes of 1-nm diameter", S Iijima and T Ichihashi *Nature, vol.* 363, p. 603 (1993); "Cobalt-catalysed growth of carbon nanotubes with single-atomic-layer walls," D S Bethune, C H Kiang, M S DeVries, G Gorman, R Savoy and R Beyers *Nature*, vol. 363, p. 605 (1993); U.S. Pat. No. 5,424,054 to Bethune et al.; Guo, T., Nikoleev, P., Thess, A., Colbert, D. T., and Smally, R. E., Chemical Physics Letters 243: 1-12 (1995); Thess, A., Lee, R., Nikolaev, P., Dai, H., Petit, P., Robert, J., Xu, C., Lee, Y. H., Kim, S. G., Rinzler, A. G., Colbert, D. T., Scuseria, G. E., Tonarek, D., Fischer, J. E., and Smalley, R. E., Science, 273: 483-487 (1996); Dai., H., Rinzler, A. G., Nikolaev, P., Thess, A., Colbert, D. T., and Smalley, R. E., Chemical Physics Letters 260: 471-475 (1996); U.S. Pat. No. 6,761,870 (also WO 00/26138) to Smalley, et. al; "Controlled production of single-wall carbon nanotubes by catalytic decomposition of CO on bimetallic Co—Mo catalysts," *Chemical Physics Letters,* 317 (2000) 497-503; U.S. Pat. No. 6,333,016 to Resasco, et al., etc. All of these references are hereby incorporated by reference.

The most preferred way of making carbon nanotubes is by catalytic growth from hydrocarbons or other gaseous carbon compounds, such as CO, mediated by supported or free floating catalyst particles.

Carbon nanotubes may also be formed as aggregates, which are dense microscope particulate structures of entangled carbon nanotubes and may resemble the morphology of bird nest, cotton candy, combed yarn or open net. Aggregates are formed during the production of carbon nanotubes and the morphology of the aggregate is controlled by the choice of catalyst support. Spherical supports grow nanotubes in all directions leading to the formation of bird nest aggregates. Combed yarn and open net aggregates are prepared using supports having one or more readily cleavable planar surfaces, e.g., an iron or iron-containing metal catalyst particle deposited on a support material having one or more readily cleavable surfaces and a surface area of at least 1 square meter per gram. Further details regarding the formation of carbon nanotube aggregates may be found in the disclosure of U.S. Pat. No. 6,143,689 to Moy; U.S. Pat. No. 5,165,909 to Tennent et al.; U.S. Pat. No. 5,456,897 to Moy et al.; Snyder et al., U.S. Pat. No. 5,707,916, filed May 1, 1991, and PCT Application No. US89/00322, filed Jan. 28, 1989 ("Carbon Fibrils") WO 89/07163, and Moy et al., U.S. Pat. No. 5,456,897 filed Aug. 2, 1994 and PCT Application No. US90/05498, filed Sep. 27, 1990 ("Battery") WO 91/05089, and U.S. Pat. No. 5,500,200 to Mandeville et al., filed Jun. 7, 1995 and U.S. Pat. No. 5,456,897 filed Aug. 2, 1994 and U.S. Pat. No. 5,569,635 filed Oct. 11, 1994 by Moy et al., all of which are assigned to the same assignee as the invention here and are hereby incorporated by reference.

Carbon nanotubes are distinguishable from commercially available continuous carbon fibers. For instance, carbon fibers have aspect ratios (L/D) of at least $10^4$ and often $10^6$ or more, while carbon nanotubes have desirably large, but unavoidably finite, aspect ratios (e.g., less than or greater than 100). Furthermore, the diameter of continuous carbon fibers, which is always greater than $1.0\mu$ and typically 5 to $7\mu$, is also far larger than that of carbon nanotubes, which is usually less than $1.0\mu$. Carbon nanotubes also have vastly superior strength and conductivity than carbon fibers.

Carbon nanotubes also differ physically and chemically from other forms of carbon such as standard graphite and carbon black. Standard graphite, because of its structure, can undergo oxidation to almost complete saturation. Moreover, carbon black is an amorphous carbon generally in the form of spheroidal particles having a graphene structure, such as carbon layers around a disordered nucleus. On the other hand, carbon nanotubes have one or more layers of ordered graphitic carbon atoms disposed substantially concentrically about the cylindrical axis of the nanotube. These differences, among others, make graphite and carbon black poor predictors of carbon nanotube chemistry.

Carbon Nanotube Structures

In addition to carbon nanotubes, carbon nanotube structures are known to be useful catalyst supports and catalysts. Carbon nanotube structures provide certain structural advantages over other known carbon catalyst supports in that more of the internal pore structures are in the form of mesopores (i.e., 2 to 50 nm) and macropores (i.e., greater than 50 nm). Furthermore, carbon nanotube structures also have greater structural strength, and thus are less likely to frit or attrit in comparison to other known carbon catalyst supports.

Carbon nanotube structures include, but are not limited to, assemblages and rigid porous structures.

a. Assemblages are carbon nanotube structures which have relatively uniform properties along one, preferably two and most desirably three dimensional axis of the three dimensional assemblage. (E.g., U.S. Pat. No. 5,691,054 hereby incorporated by reference). Generally, assemblages (including but not limited to mats and plugs) are formed by de-aggregating carbon nanotube aggregates, and then reassembling them to form assemblages which have uniform properties over a greater range of distance than the original aggregates. Nanotube mats or assemblages have been prepared by dispersing carbon nanotubes in aqueous or organic mediums and then filtering the nanotubes to form a mat or assemblage. Mats and plugs have also been prepared by forming a gel or paste of nanotubes in a fluid, e.g. an organic solvent such as propane and then heating the gel or paste to a temperature above the critical temperature of the medium, removing the supercritical fluid and finally removing the resultant porous mat or plug from the vessel in which the process has been carried out. A gluing agent may be present during the step of mat or plug formation. As the assemblage dries, the glue will concentrate at the nanotube intersections. Preferred gluing agents or binders include cellulose-based polymers, hydroxyl ethyl cellulose, carboxyl methyl cellulose, cellulose, carbohydrates, polyethylene, polystyrene, nylon, polyurethane, polyester, polyamides, poly(dimethylsiloxane), acrylic polymers and phenolic resins. Preferably, the polymers are free of alkali metal salts such as sodium or potassium salts.

b. Rigid porous structures are formed by either linking the individual functionalized carbon nanotubes together without the use of a linking molecule, or by gluing carbon nanotube aggregates together with a gluing agent. U.S. Pat. No. 6,099,965, hereby incorporated by reference, discloses that certain functionalized nanotubes become self adhesive after an appropriate thermal treatment. The carbon nanotubes are functionalized, for example, by contacting them with an appropriate reagent (e.g., WO 97/32571, U.S. Pat. No. 6,203,814, all of which are herein incorporated by reference), or by contacting them with an oxidizing agent such as potassium chlorate ($KClO_3$), sulfuric acid ($H_2SO_4$), nitric acid ($HNO_3$), persulfate, hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference). The oxidized nanotubes are believed to form ester, anhydride, lactone and ether bonds between themselves.

When a gluing agent is employed, the nanotubes may be unfunctionalized and may be used as individual tubes or in their aggregated form. Preferred gluing agents or binders include cellulose-based polymers, hydroxyl ethyl cellulose, carboxyl methyl cellulose, cellulose, carbohydrates, polyethylene, polystyrene, nylon, polyurethane, polyester, polyamides, poly(dimethylsiloxane), acrylic polymers and phenolic resins. Preferably, the polymers are free of alkali metal salts such as sodium or potassium salts.

Forming generally accepted forms of industrial catalyst support includes pelletization, extrusion, compaction or powder agglomeration as indicated in "Catalyse de Contact" edited by J. F. Le Page, Paris, 1978, hereby incorporated by reference. Rigid porous structures may advantageously be made by extruding a paste like suspension of functionalized nanotubes or a mixture of as made aggregates and gluing agent, (optionally admixed with a liquid vehicle) followed by a calcinations step to drive off conveying liquids and either cross link the functionalized nanotubes or to pyrolize the gluing agent.

While activated charcoals and other materials have been used as catalysts and catalyst supports, none have heretofore had all of the requisite qualities of high surface area, porosity, pore size distribution, resistance to attrition and purity for the conduct of a variety of selected petrochemical and refining processes as compared to carbon nanotube structures. Furthermore, unlike carbon nanotube structures, much of the surface area in activated charcoals and other materials is in the form of inaccessible micropores.

Therefore, it would be desirable to provide a supported catalyst comprising a carbon nanotube structure with well or evenly dispersed metal catalysts therein, the supported catalyst consequently having highly accessible surface area, high porosity, and attrition resistance, and which are substantially micropore free, highly active, highly selective and are capable of extended use with no significant deactivation.

SUMMARY OF THE INVENTION

A new method for preparing supported catalysts is provided comprising the steps of loading metal catalyst onto carbon nanotubes to form metal loaded carbon nanotubes; and forming a carbon nanotube structure from said metal loaded carbon nanotubes.

Preferably, the supported catalysts are prepared by a process comprising the steps of functionalizing carbon nanotubes with a functionalizing agent to form functionalized carbon nanotubes; loading metal catalyst onto said functionalized carbon nanotubes to form metal loaded carbon nanotubes; and forming a carbon nanotubes rigid porous structure from said metal loaded carbon nanotubes. Desirably, the dispersion of the metal catalysts in the carbon nanotube structure is equal to or greater than the dispersion of the metal catalysts in the original metal loaded carbon nanotubes.

The most straightforward functionalization, especially useful for multi-wall nanotubes is oxidation. Useful oxidizing agents include, but is not limited to, potassium chlorate, sulfuric acid, nitric acid ($HNO_3$), persulfate, hydrogen peroxide ($H_2O_2$), $CO_2$, $O_2$, steam, $N_2O$, NO, $NO_2$, $O_3$, or $ClO_2$.

Catalysts or catalyst precursors useful in the methods of the present invention include, but are not limited to, metals such as ruthenium, osmium, rhodium, iridium, palladium, platinum, silver, gold or a mixture thereof, as well as oxides, halides, carbides, nitrides, phosphides and sulfides of other transition metals including but not limited to Ti, V, Cr, Mn, Fe, Co, Ni, Cu, Zn, Y, Zr, Nb, Mo, La, Ce, W or combinations thereof. The metal catalysts or metal catalyst precursors may be loaded onto the nanotubes by any known method, such as ion exchange, impregnation, or incipient wetness, precipitation, physical or chemical adsorption or co-precipitation. In the preferred embodiment, the metal catalysts are predeposited or loaded onto the functionalized carbon nanotubes by ion exchange, i.e. mixing a solution containing salts of said metal catalysts with the functionalized carbon nanotubes, allowing the salts to react with the functional groups of the functionalized nanotubes and evaporating the remaining solution (e.g., the excess solvent from the solution). Alternatively, the metal catalysts are predeposited or loaded onto carbon nanotubes by impregnation, or incipient wetness, i.e. wetting a mass of carbon nanotubes with a solution of metal salts and evaporating the solvent. Alternatively, metal salts may be caused to precipitate from solution in the presence of a mass of carbon nanotubes causing said precipitated metal salts to physically or chemically adsorb on said nanotubes, followed by evaporation of the solvent.

Preferably, the carbon nanotube structure is a rigid porous structure formed by extruding the metal loaded carbon nanotubes. The metal loaded rigid porous structure may be further calcined to improve structural integrity.

Alternatively, the structure may be an assemblage formed by filtering a suspension of metal loaded carbon nanotubes. These conveniently take the form of thin mats especially useful in electrocatalysis. The metal loaded assemblage may be further calcined to improve structural integrity.

Alternatively, the carbon nanotube structure is a rigid porous structure formed by extruding said metal loaded carbon nanotubes with gluing agents or binders selected from the group consisting of cellulose-based polymers, hydroxyl ethyl cellulose, carboxyl methyl cellulose, cellulose, carbohydrates, polyethylene, polystyrene, nylon, polyurethane, polyester, polyamides, poly(dimethylsiloxane), acrylic polymers and phenolic resins. Preferably, the polymers are free of alkali metal salts such as sodium or potassium salts. An assemblage can also be formed by filtration of metal loaded carbon nanotubes from a suspension in which a gluing agent is also present. As the assemblage dries, the gluing agent wick to the nanotubes intersections. Again, these assemblage are conveniently in the form of mats useful for electrocatalysis.

Any of these glued structures are desirably rigidized by calcining. Calcination may be carried out in the presence of absence of air. When air is present, calcinations temperature is limited to less than about 300° C. Calcination in inert atmosphere may be carried out at temperatures of about 300° C. to about 900° C.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTION OF THE DRAWINGS

The accompanying drawings, which are incorporated in and constitute a part of the specification, illustrate an exemplary embodiment of the present invention.

DETAILED DESCRIPTION OF THE PREFERRED EMBODIMENT

Figure 1:
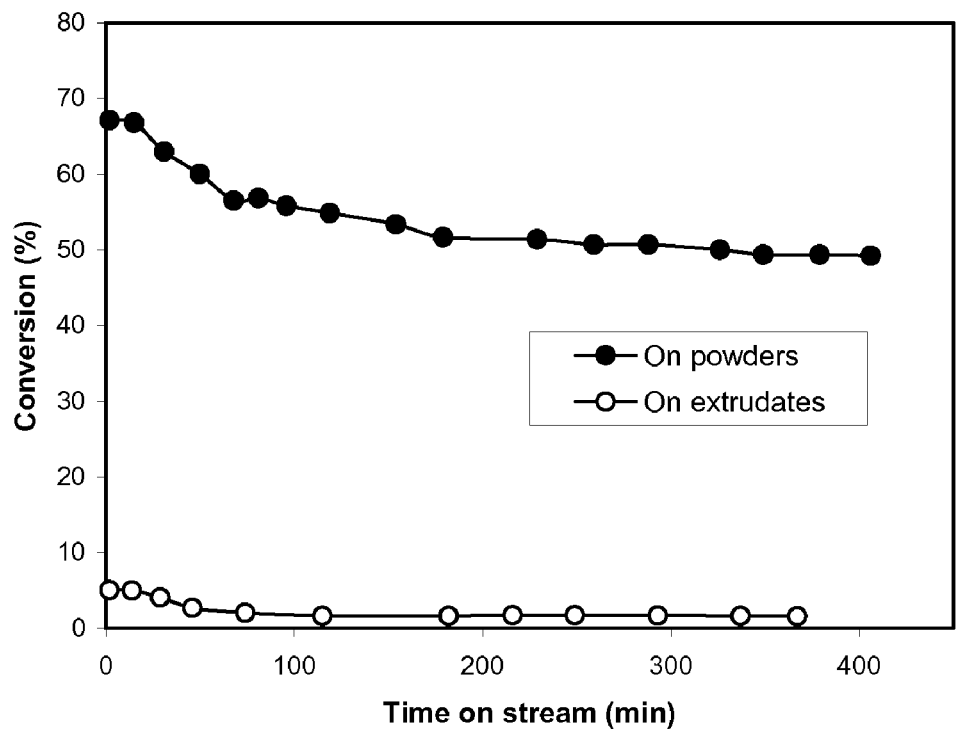
FIG. 1 displays the results of the hydrogenation of cyclohexene using 0.5 wt % supported Pd catalysts in powder and extrudate form as prepared in accordance with Example 2.

All patents, patent applications, and patent publications referred to herein are incorporated by reference in their entirety.

DEFINITIONS

The terms "nanotube", "nanofiber" and "fibril" are used interchangeably to refer to single walled or multiwalled carbon nanotubes. Each refers to an elongated structure preferably having a cross section (e.g., angular fibers having edges) or a diameter (e.g., rounded) less than 1 micron (for multiwalled nanotubes) or less than 5 nm (for single walled nanotubes). The term "nanotube" also includes "buckytubes", and fishbone fibrils.

"Aggregate" refers to a dense, microscopic particulate structures of entangled carbon nanotubes.

"Assemblage" refers to structures having relatively or substantially uniform physical properties along at least one dimensional axis and desirably having relatively or substantially uniform physical properties in one or more planes within the assemblage, i.e., they have isotropic physical properties in that plane. The assemblage may comprise uniformly dispersed individual interconnected nanotubes or a mass of connected aggregates of nanotubes. In other embodiments, the entire assemblage is relatively or substantially isotropic with respect to one or more of its physical properties. The physical properties which can be easily measured and by which uniformity or isotropy are determined include resistivity and optical density.

"Graphenic" carbon is a form of carbon whose carbon atoms are each linked to three other carbon atoms in an essentially planar layer forming hexagonal fused rings. The layers are platelets having only a few rings in their diameter or ribbons having many rings in their length but only a few rings in their width.

"Graphitic" carbon consists of layers which are essentially parallel to one another and no more than 3.6 angstroms apart.

"Internal structure" refers to the internal structure of a carbon nanotube structure including the relative orientation of the carbon nanotubes, the diversity of and overall average of nanotube orientations, the proximity of the nanotubes to one another, the void space or pores created by the interstices and spaces between the fibers and size, shape, number and orientation of the flow channels or paths formed by the connection of the void spaces and/or pores. According to another embodiment, the structure may also include characteristics relating to the size, spacing and orientation of aggregate particles that form the assemblage. The term "relative orientation" refers to the orientation of an individual nanotube or aggregate with respect to the others (i.e., aligned versus nonaligned). The "diversity of" and "overall average" of nanotube or aggregate orientations refers to the range of nanotube orientations within the structure (alignment and orientation with respect to the external surface of the structure).

"Isotropic" means that all measurements of a physical property within a plane or volume of the structure, independent of the direction of the measurement, are of a constant value. It is understood that measurements of such non-solid compositions must be taken on a representative sample of the structure so that the average value of the void spaces is taken into account.

"Macropore" refers to a pore which has a diameter of greater than or equal to 50 nm.

"Mesopore" refers to a pore which has a diameter of greater than or equal to 2 nm but less than 50 nm.

"Micropore" refers to a pore which has a diameter of less than 2 nm.

"Nonuniform pore structure" refers to a pore structure occurring when individual discrete nanotubes are distributed in a substantially nonuniform manner with substantially nonuniform spacings between nanotubes.

"Physical property" means an inherent, measurable property of the porous structure, e.g., surface area, resistivity, fluid flow characteristics, density, porosity, etc.

"Pore" traditionally refers to an opening or depression in the surface of a catalyst or catalyst support. Catalysts and catalyst supports comprising carbon nanotubes lack such traditional pores. Rather, in these materials, the spaces between individual nanotubes behave as (and are referred to herein as) pores, and the equivalent pore size of nanotube aggregates can be measured by conventional methods (porosimetry) of measuring pore size and pore size distribution. By varying the density and structure of aggregates, the equivalent pore size and pore size distribution can be varied.

"Relatively" means that 95% of the values of the physical property when measured along an axis of, or within a plane of or within a volume of the structure, as the case may be, will be within plus or minus 20% of a mean value.

"Substantially" or "predominantly" mean that 95% of the values of the physical property when measured along an axis of, or within a plane of or within a volume of the structure, as the case may be, will be within plus or minus 10% of a mean value.

"Surface area" refers to the total surface area of a substance measurable by the BET technique as known in the art, a physisorption technique. Nitrogen or helium can be used as absorbents to measure the surface area.

"Uniform pore structure" refers to a pore structure occurring when individual discrete nanotubes or nanofibers form the structure. In these cases, the distribution of individual nanotubes in the particles is substantially uniform with substantially regular spacings between the nanotubes. These spacings (analogous to pores in conventional supports) vary according to the densities of the structures.

Methods of the Preferred Embodiments

The present invention provides a new process for preparing supported catalysts comprising a metal loaded carbon nanotube structure. The supported catalysts prepared in accordance with the preferred embodiment results in a better distribution and better dispersion of the metal catalysts within the carbon nanotube structure, and consequently can yield better catalytic activity.

The method of the preferred embodiment comprises loading the metal catalyst onto carbon nanotubes and forming a carbon nanotube structure from the loaded carbon nanotubes. As used throughout this application, the term "metal catalyst" includes precursors of such metal catalyst. That is, metal catalyst includes metals such as ruthenium, osmium, rhodium, iridium, palladium, platinum, silver, gold or a mixture thereof, as well as oxides, halides, carbides, nitrides, phosphides and sulfides of other transition metals including but not limited to Ti, V, Cr, Mn, Fe, Co, Ni, Cu, Zn, Y, Zr, Nb, Mo, La, Ce, W or combinations thereof.

Preferably, the carbon nanotubes are functionalized before loading the metal catalysts, and the carbon nanotube structure is a rigid porous structure formed by extruding the metal loaded carbon nanotubes. The carbon nanotube structure containing the metal catalysts represent the supported catalyst. When metal catalysts (in the form of precursors of metal catalyst) are loaded onto the carbon nanotube, various post-extrusion treatment such as calcinations, reduction, carburization, nitrodization, phosphurization and sulphurization can be applied to obtain the desired catalyst composition.

As such, the terms supported catalyst and supported metal catalyst as used in this application may refer to any of: the inert support with metal salt (or active material precursor) deposited thereon; the same material after calcination or other pre-reaction treatment; or the inert support with active material thereon having whatever composition it takes on in the reaction zone.

Functionalization

In the preferred embodiment, carbon nanotubes (whether produced in the form of discrete nanotubes or as-made aggregates, or mixture of both) are predeposited or loaded with metal catalysts before the metal loaded carbon nanotubes are extruded or otherwise made into a carbon nanotube structure. All types of carbon nanotubes as produced, whether it be single walled or multi walled, can be used.

A preferred method to accomplish the predeposition or loading of the metal catalyst onto the carbon nanotube is to first functionalize the carbon nanotube surface before mixing with the metal catalyst or salt thereof. Functionalizing the carbon nanotubes results in the substitution of functional groups such as oxygen containing moieties onto the surface of the carbon nanotubes, which consequently results in better attachment of the metal catalyst to the carbon nanotube surface (whether by adsorption, hydrogen bond, adhesion, electrostatic attraction, covalent bond, absorption, van der Waals force, or any other mechanism which may occur to secure, support, hold or otherwise keep the metal catalyst onto the carbon nanotube surface). A good survey article on functionalization, hereby included in its entirety by reference, covering both single wall and multiwall tubes is: Hirsch, A. and Vostrowsky, O., "Functionalization of Carbon Nanotubes," Topics in Current Chemistry, (2005)245:193-237.

Functionalization can be accomplished, for example, by contacting the carbon nanotubes with an appropriate reagent (e.g., WO 97/32571, U.S. Pat. No. 6,203,814, all of which are herein incorporated by reference), or preferably by contacting them with an oxidizing agent such as potassium chlorate, sulfuric acid, nitric acid ($HNO_3$), persulfate, hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference).

Where the carbon nanotubes are in the form of aggregates, it is preferred to both break up or de-aggregate the aggregates and functionalize them. Such tasks can be accomplished concurrently by oxidizing the carbon nanotube aggregates, for example, by contacting them with an oxidizing agent such as potassium chlorate, sulfuric acid, nitric acid ($HNO_3$), persulfate, hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference). Breaking up of the as-produced aggregates into individual carbon nanotubes is preferable (although not necessary) in order to permit a more thorough distribution of functional groups onto the carbon nanotube surfaces, as well as to easier facilitate the creation of other carbon nanotube structures such as assemblages, mats, rigid porous structures, etc. Hence, when oxidizing agents are used, the terms "functionalized" and "oxidized" may be used interchangeably.

In an exemplary embodiment, the carbon nanotubes are oxidized by contacting the nanotubes with ozone under conditions suitable to achieve the desired functionalization (and deaggregation in the case of carbon nanotubes which are in the form of aggregates). Further details are provided in U.S. Provisional Application No. 60/621,132, filed Oct. 22, 2004 entitled "OZONOLYSIS OF CARBON NANOTUBES," herein incorporated by reference. A particularly useful functionalization method especially for single wall tubes is cycloaddition. See, for example, Holzinger, M., et al. "[2+1] cycloaddition for cross linking SWCNTs," Carbon 42 (2004) 941-947 and Georgakilas, V. et al. "Organic Functionalization of Carbon Nanotubes," JACS Communications, 124 (2002) 760, 761, both of which are hereby included by reference. Alternatively, single wall tubes can be functionalized as described in U.S. patent application Ser. No. 10/875,435, filed Jun. 23, 2004.

Another useful purpose served by functionalization is that the functional groups which remain after the deposition or loading of the metal catalyst permit the individual carbon nanotubes to be linked via those remaining functional groups or sites to form additional carbon nanotube structures such as assemblages, rigid porous structures, etc. The remaining functional groups may be linked or cross linked using known techniques, such as crosslinking agents, calcination, pyrolysis, carbonization, etc.

The subsequent creation of these additional carbon nanotube structures can also be accomplished using any of the following methods or combinations: extrusion, gluing agents, cross linking, pyrolysis, carbonization, etc. (e.g., U.S. Pat. No. 6,031,711, U.S. Pat. No. 6,099,965, etc., all of which are hereby incorporated by reference).

Predeposition or Loading of Metal Catalysts

Preferred metal catalysts include ruthenium, osmium, rhodium, iridium, palladium, platinum, silver, gold or a mixture thereof, as well as oxides, halides, carbides, nitrides, phosphides and sulfides of other transition metals including but not limited to Ti, V, Cr, Mn, Fe, Co, Ni, Cu, Zn, Y, Zr, Nb, Mo, La, Ce, W or combinations thereof. More preferably, the metal catalyst is palladium, platinum, or a mixture thereof.

Where the carbon nanotubes are previously functionalized, predeposition or loading of the metal catalyst onto the carbon nanotube surface can be accomplished by mixing the metal catalyst material with the carbon nanotubes. Due to the change in carbon nanotube surface chemistry caused by the presence of functional groups, the metal catalyst may be held or supported onto the carbon nanotube surface via adsorption, hydrogen bond, adhesion, electrostatic attraction, covalent bond, absorption, van der Waals force or any other mechanism which may occur to secure, support, hold or otherwise keep the metal catalyst onto the carbon nanotube surface. It is preferred, where the functional groups are used to subsequently link the individual nanotubes to form carbon nanotube structures, that the amount of metal deposited or loaded onto the carbon nanotube surface not exceed or otherwise "use up" the functional groups needed to hold or support the metal catalyst on the carbon nanotube surface. In other words, it is preferred that there be free functional groups remaining on the carbon nanotube surface after the predeposition or loading of the metal catalyst.

Furthermore, the metal catalysts can be introduced to the carbon nanotubes in the form of a salt or derivative, or in the form of metal-containing micelles. As discussed earlier, these forms are often referred to as precursors of the metal catalyst, but are included in the term metal catalysts as used in this application. For example, the metal can be introduced to the carbon nanotube in the form of a water-soluble salt such as nitrate, acetate or chloride. Metal catalysts which have been loaded onto the carbon nanotube as salts are then preferably reduced via a reducing agent to further accomplish the deposition of the metal catalyst onto the carbon nanotube surface. Additionally, it is preferred in the case of metal catalysts introduced as a metal salt in a solution, that the solvent component of the solution be subsequently evaporated.

Any conventional mixing devices or mechanism can be employed. Factors such as mixing speed or time can be adjusted accordingly to facilitate the contact of the carbon nanotube and the metal catalyst, and to spread the metal catalyst thoroughly throughout the mixture so as to create a better distribution of metal catalysts on the carbon nanotubes.

Additional methods for accomplishing predeposition of the metal catalyst onto the carbon nanotube surface include, but is not limited to, impregnation, incipient wetness, ion exchange, precipitation, physical or chemical adsorption and co-precipitation.

Carbon nanotubes which have metal catalysts deposited on them will be referred to as "predeposited carbon nanotubes" or "metal loaded carbon nanotubes."

Structures

Once the metal catalysts have been deposited onto the surfaces of the carbon nanotubes, these metal loaded carbon nanotubes are then used to form carbon nanotube structures such as assemblages, rigid porous structures, etc. using conventional methods as previously described. These methods may include extrusion, pelletizing, compaction, etc.

In the preferred embodiment, the carbon nanotube structure is formed by extruding the metal loaded carbon nanotubes to create a rigid porous carbon nanotube structure (also known as extrudates). Extrusion can be accomplished using any conventional extrusion device such as a die, single screw or twin screw extruder. The speed or rate of extrusion will vary depending on the amount of materials to be extruded.

The above-described rigid porous structures are formed by causing the nanotubes to form bonds or become glued with other nanotubes at the nanotube intersections. The bonding can be induced by chemical modification of the surface of the nanotubes to promote bonding, by adding "gluing" agents and/or by pyrolyzing the nanofibers to cause fusion or bonding at the interconnect points. U.S. Pat. No. 6,099,965 to Tennent, herein incorporated by reference, describes processes for forming rigid porous structures from carbon nanotubes.

The metal loaded carbon nanotubes are introduced to the extruder in the form of a slurry. Preferred slurry carriers include water and other non-reactive solvents. Extrusion subjects the metal loaded carbon nanotubes to compressive and shear forces which creates a wet product in a commercially desirable shape. The extruder effluent is normally chopped into a convenient pellet shape before drying and calcination.

In accordance with the preferred embodiment, because the metal catalysts have already been deposited, spread and distributed throughout the carbon nanotubes in its discrete form prior to creating the carbon nanotube structure, the result is that the carbon nanotube structure itself would also have a greater and/or more even distribution of metal catalyst throughout and within the structure. Furthermore, because of the porosity characteristics (e.g., more meso and macropores) of the carbon nanotube structure, the accessibility and availability of the metal catalyst for reactions is greater than in other support catalyst structures previously prepared. This availability improvement is especially significant for liquid phase reactions, where larger pores are needed in order for the liquid phase reactants to reach the internal metal catalysts.

Furthermore, the carbon nanotube structure prepared by the preferred embodiment will also have at least the same or greater amount of metal catalyst dispersion compared to the metal loaded carbon nanotubes prior to extrusion. Catalyst dispersion measures the percent of the metal catalyst particle that is available for reaction. In other words, a 40% metal catalyst dispersion means that only 40% of that metal catalyst particle is available for reaction—the remaining 60% is unavailable for reaction (e.g., it is bound to the carbon nanotube surface, the middle mass of the particle is unavailable as well, etc.) Catalyst dispersion may be measured by determining the amount of gas such as carbon monoxide adsorbed on the carbon nanotube surface. Thus, in the preferred embodiment, for example, metal loaded carbon nanotubes having a 50% metal catalyst dispersion prior to extrusion will, in accordance with the preferred embodiment, have at least 50% or greater metal catalyst dispersion in the resulting carbon nanotube structure after extrusion. Consequently, supported catalysts (i.e., the carbon nanotube structure containing the metal catalyst) prepared according to the preferred embodiment are superior to other known supported catalysts where catalyst dispersion may undesirably decrease (e.g., shear forces cause individual particles to lump together, thereby reducing the amount of the catalyst particle that is available to participate in a chemical reaction).

Once extruded, the extrudates may be dried and calcined. Calcination may be done in air or inert gases at temperatures ranging from 100-300° C. The extrudates may be further reduced with hydrogen or reacted with other reagents to yield carbides, nitrides, phosphides or sulphides. Alternatively, the extrudate may be pyrolyzed or carbonized at temperatures greater than 400° C. to cause fusion or bonding at the interconnect points, followed by passivation at room temperature.

In another alternative embodiment, gluing agents and/or binders may be used to further improve the mechanical strength of the extrudate by, for example, promoting bonding among the carbon nanotubes within the rigid porous structure. Specifically, gluing agents or water soluble polymeric binders can be added to the slurry before extruding the metal loaded carbon nanotubes. Examples of these binders include cellulose-based polymers such as hydroxyl ethyl cellulose and carboxyl methyl cellulose. Other examples of gluing agents or binders include, without limitation, cellulose, carbohydrates, polyethylene, polystyrene, nylon, polyurethane, polyester, polyamides, poly(dimethylsiloxane), phenolic resins, acrylic polymers and the like. Preferably, the polymers are free of alkali metal salts such as sodium or potassium salts.

Addition of gluing agents can also be coupled with dispersing metal precursors in polymeric reagents to form metal nanoclusters, also known as metal loaded micelles. These micelles are generated from an amphiphilic block copolymer such as poly(styrene-block-acrylic acid) (PS-b-PAA) in solution which are capable of self-organizing into ordered structures on surfaces. This allows for the creation of quasi-hexagonal arrays of PAA spheres within in a PS matrix. The carboxylic acids groups in the PAA domains can be utilized in an ion-exchange protocol to selectively seize metal ions. The resulting metal-containing nanoclusters are nearly monodisperse in size (diameter <10 nm) and patterned at a density of approximately $10^{11}$ particles per $cm^2$. Furthermore, it is possible to control the cluster size and spacing by altering the molecular weight of the block copolymer, for example, choose a lower molecular weight polymer will consequently result in the formation of smaller micelle size which will further translate into smaller metal cluster size.

In the preferred embodiment, the supported catalyst comprises a rigid porous structure substantially free of micropores, having a surface area greater than 100 $m^2$/gm and a crush strength greater than 5 psi for extrudates of ⅛ inch in diameter. Preferably the surface area of the rigid porous structure is greater than 200 $m^2$/gm, more preferably between 250 and 1000 $m^2$/gm. Carbon nanotube extrudates may have densities greater that 0.2 gm/$cm^3$, preferably greater than 0.3 gm/$cm^3$, which can be controlled by the density of the extrusion paste. A preferred range includes 0.3 gm/$cm^3$-1.0 gm/$cm^3$. The extrudates have liquid absorption volumes greater than about 0.7 $cm^3$/gm.

It is further preferred that the extrudates have an equal or higher level of metal catalyst dispersion compared to the metal loaded carbon nanotubes prior to extrusion. The metal catalyst dispersion can be measured using conventional chemisorption (i.e., chemical adsorption) techniques, and are often referred to as "apparent" dispersion. For example, in measuring the dispersion of a metal catalyst such as palladium in a carbon nanotube structure, carbon monoxide is usually used since molecules of CO are known to bond to the Pd atom such that the apparent dispersion of the Pd catalyst throughout the carbon nanotube may be calculated or measured.

It has been discovered that self-supported catalysts comprising carbon nanotube structures have high internal void volumes that ameliorate the plugging problem encountered in various processes. Moreover, the preponderance of large pores obviates the problems often encountered in diffusion or mass transfer limited reactions. The high porosities further increases catalyst life.

These catalytic compositions can be used as catalysts to catalyze reactions such as hydrogenation, hydrodesulfurisation, hydrodenitrogenation, hydrodemetallisation, hydrodeoxygenation, hydrodearomatization, dehydrogenation, hydrogenolysis, isomerization, alkylation, dealkylation, transalkylation, hydroformylation, water-shift, Fischer-Trosch, COx-free hydrogen production, ammonia synthesis, electrocatalysis, oxidation, florination, and $NO_x$ reduction.

EXAMPLES

The examples are illustrative and not to be considered restrictive of the scope of the invention. Numerous changes and modification can be made with respect to the invention. The materials used in the examples herein are readily commercially available.

In all of the experiments which follow, aggregates of carbon nanotubes as manufactured by Hyperion Catalysis International of Cambridge, Mass. were used. The aggregates of carbon nanotubes were of the cotton candy ("CC") morphology also known as combed yarn ("CY").

Terms

Where convenient, the following terms may be used in the following examples:

"$HNO_3$ oxidized CC carbon nanotube powders" refer to samples of CC carbon nanotube aggregates which were subsequently oxidized with $HNO_3$, and then ground into powder form.

"Pd/nanotube extrudate" refers to samples of extrudates which have been loaded with Pd metal catalyst. The Pd catalyst may be loaded before or after the extrudate was formed, depending on the process used in the example.

"Pd/nanotube powder" refers samples of oxidized carbon nanotubes which have been loaded with Pd, and have not yet been extruded.

"Pd/nanotube pellets" refers to samples of pellets which have been loaded with Pd metal catalyst. The Pd catalyst may be loaded before or after the pellet was formed, depending on the process used in the example.

Example 1

$HNO_3$ oxidized CC carbon nanotube powders were created by pre-grinding $HNO_3$ oxidized CC carbon nanotubes and sieved with a 20 mesh sieve. 70 ml of $PdAc_2$/acetone solution containing 0.148 g of $PdAc_2$ was poured into a porcelain crucible with 7.0 g of $HNO_3$ oxidized CC carbon nanotube powders to create a slurry, which was then stirred with a magnetic stirrer. After vaporizing most of the solvent at room temperature, the slush-like cake was dried under vacuum at 100° C. for 1-2 hrs.

The extrusion procedure was carried out with a Brabender device. (PLASTI-CORDER® ¾" Laboratory Extruder. The screw has 25 flites and a compression ratio of 3:1). 14.0 g of deionized ("DI") water were added to 6.0 g of 1 wt % Pd/nanotube powders at room temperature. The solid content in this dry-look mixture is around 30%. The mixture was extruded at room temperature and 30 RPM, and resulting extrudates were dried at 100-110° C. in a vacuum oven.

Two batches of extrudates were made from two different batches of $HNO_3$ oxidized CC nanotubes. The properties of these two batches of carbon nanotubes are listed in the following Table 1. The two batches were made under the same conditions. However, Batch 1 was kept as wet cakes after the nitric acid oxidation process, then dried before loading Pd. Batch 2 was made into an extrudate and then ground before loading Pd.

TABLE 1

HNO$_3$-oxidized CC nanotube powders

| Batch | Titer (meqv/g) | Appearance |
|---|---|---|
| 1 | 1.0 | Wet cake, freshly dried before loading Pd |
| 2 | 1.0 | Extrudates, ground to powders |

The physical properties of Pd/nanotube extrudates such as apparent Pd dispersion and particle size were examined using carbon monoxide (CO) chemisorption at room temperature assuming one CO molecule adsorbed on one Pd atom. Prior to CO chemisorption, the sample was in situ reduced under flowing H$_2$ at 300° C. for 2 hrs, followed by 30 min evacuation at 300° C. The results are presented in Table 2.

TABLE 2

| Batch # | Pd loading (wt %) | Appearance | Finger Smash Test | Pd dispersion (%) | Pd Particle size (nm) |
|---|---|---|---|---|---|
| 1 | 1 | Powder | N/A | 49.3 | 2.3 |
|   |   | Extrudate | Can | 46.2 | 2.4 |
| 2 | 1 | Powder | N/A | 50.1 | 2.2 |
|   |   | Extrudate | Can't | 52.6 | 2.1 |

As shown in Table 2, both batches of the Pd/nanotube powder prior to extrusion had very similar apparent Pd dispersions (e.g., 49.3% vs. 50.1%). After the batches were extruded, the apparent Pd dispersion differed between the Pd/nanotube extrudates (e.g., 46.2% vs. 52.6%), but within experimental error. More importantly, these data show that nanotubes with Pd pre-deposition can be fabricated into extrudate with essentially no loss in dispersion.

It was further observed that the two batch extrudates also exhibited different strength. The Batch 1 extrudate could be smashed by a finger and thus, did not pass finger smash test. On the other hand, the Batch 2 extrudate could not be smashed by a finger, indicating that it is a stronger structure.

To further examine structural strength, the batch extrudates were subjected to crush strength tests. The batches were first calcined under H$_2$ for 2 hours. To eliminate the possibility that calcination under H$_2$ might remove some oxygen functional groups and consequently weaken crush strength, calcination under Ar was also carried out for a sample from Batch 1, the already weaker of the two batch extrudates. The results are reported in Table 3.

TABLE 3

| Batch # | Calcination | Weight loss (wt) | \multicolumn{7}{c}{Crush strength (Lb/in)} | Average | Deviation |
|---|---|---|---|---|---|---|---|---|---|---|---|

| Batch # | Calcination | Weight loss (wt) | 1 | 2 | 3 | 4 | 5 | 6 | 7 | Average | Deviation |
|---|---|---|---|---|---|---|---|---|---|---|---|
| 1 | 300° C./H$_2$/2 hr | 9.2 | 0.36 | 0.33 | 0.39 | 0.25 | 0.33 |  |  | 0.33 | 0.05 |
|   | 300° C./Ar/2 hr | 8.4 | 0.3 | 0.5 | 0.4 | 0.4 | 1.3 | 0.7 | 0.4 | 0.6 | 0.3 |
| 2 | 300° C./H$_2$/2 hr | 7.0 | 17 | 8 | 5 | 4 | 13 | 1 | 2 | 7 | 6 |

Since the crush strength for the Batch 1 extrudates calcined under Ar was greater than the crush strength for the Batch 1 extrudates calcined under H$_2$, these results confirm that calcination under H$_2$ can cause a decline of crush strength.

Table 3 confirms that the Batch 2 extrudates have higher crush strengths and thus are structurally stronger than the Batch 1 extrudates. The Batch 2 extrudates have an average crush strength around 7 lb/in, although with a large standard deviation.

To further study the effect of Pd loading on crush strength, extrudates were made from Batch 2 without loading the Pd catalyst. The crush strength of the extrudates made from Batch 2 nanotubes with and without Pd loading were examined, and the results are displayed in Table 4:

TABLE 4

| Batch # | Calcination | Weight loss (wt) | 1 | 2 | 3 | 4 | 5 | 6 | 7 | Average | Deviation |
|---|---|---|---|---|---|---|---|---|---|---|---|
| 2 w/o Pd | 300° C./Ar/2 hr | 5.1 | 25 | 18 | 3 | 4 | 10 | 6 | 22 | 13 | 9 |
| 2 | 300° C./H$_2$/2 hr | 7.0 | 17 | 8 | 5 | 4 | 13 | 1 | 2 | 7 | 6 |

The results of Table 4 indicate that the Pd/nanotube extrudates of Batch 2 have lesser crush strength than nanotube extrudates of Batch 2 which do not have any Pd loading.

Example 2

Comparison between the following two supported catalysts were made: (a) extrudates which have been loaded with Pd after extrusion vs. (b) CC nanotube powders which have been loaded with Pd and not extruded.

Extrudates were made from plain CC nanotubes with PAM-3K polymer binder, and calcined in Ar at 600° C. for 2 hrs. The extrudates were then oxidized with ozone in gas phase for 48 hrs at room temperature. The acid titer exhibited upon titration was about 0.968 meq/g. Pd was loaded on the extrudates by ion exchange in Pd(NH$_3$)$_4$(NO$_3$)$_2$ solution at room temperature. The nominal loading of Pd is about 0.5 wt %.

Supported catalysts comprising Pd catalyst supported on powder CC nanotubes were made in a similar way. Namely, powder CC nanotubes were oxidized with ozone in gas phase for 48 hrs at room temperature. The acid titer exhibited upon titration was about 1.35 meq/g. Pd was loaded on the powder by ion exchange in Pd(NH$_3$)$_4$(NO$_3$)$_2$ solution at room temperature. The nominal loading of Pd is about 0.5 wt %.

The apparent Pd dispersion in the two types of supported catalysts were measured by CO chemisorption at room temperature. The measurement was as follows: 37.4% for Pd/nanotube extrudates; 47.9% for supported Pd/nanotube powders.

Figure 2:
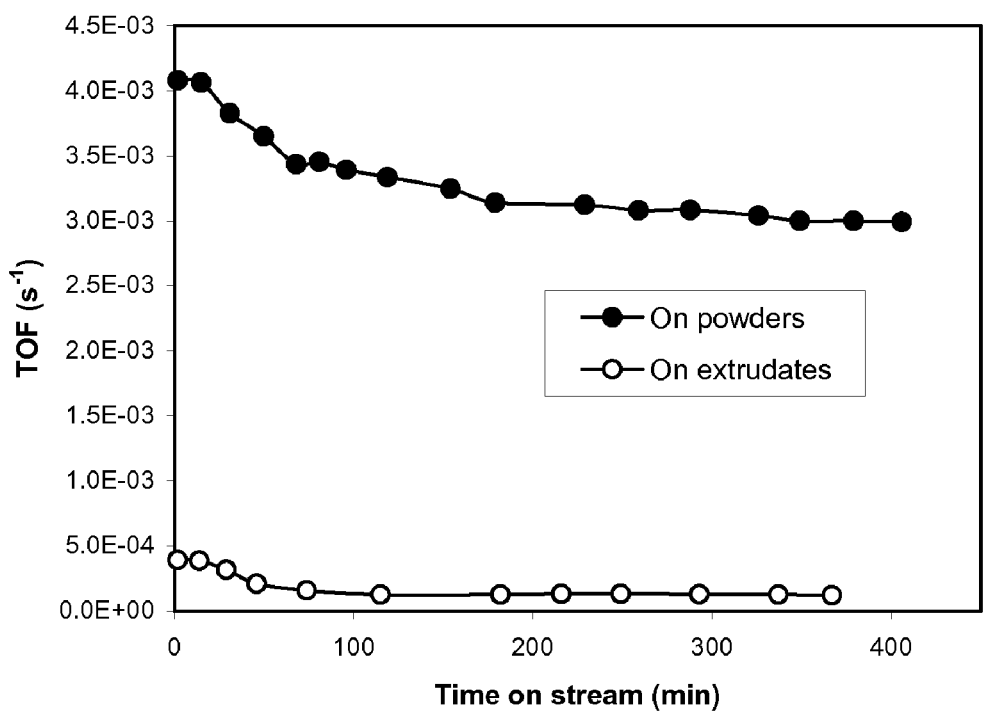
FIG. 2 displays the results of the hydrogenation of cyclohexene using 0.5 wt % supported Pd catalysts in powder and extrudate form as prepared in accordance with Example 2.

Next, catalytic activity of the two supported catalyts in cyclohexene hydrogenation was examined. The Pd extrudates were crushed into granules of 20-40 meshes, and reduced in situ with 40 ml/min of $H_2$ at 300° C. for 2 hr. The Pd/nanotube powders were not altered. 10 mg of each supported catalyst were loaded in the reactor and the cyclohexene hydrogenation was conducted at ambient temperature and pressure. Cyclohexene was bubbled into the reactor with 20 ml/min of $H_2$ and 40 ml/min of Ar to balance the total flow. The ratio of $H_2$ to Ar was therefore 1 to 2. The results are shown in FIGS. 1 and 2.

The difference in performance between the catalysts is more dramatic than one would expect from the difference in dispersion. Thus, not only is attainment of high dispersion on preformed extrudate problematical, (37.4 vs 47.9%), but reaction performance is poorer than can be accounted for by the dispersion difference alone. Because Pd metal catalysts were loaded onto the extrudate (instead of onto the carbon nanotubes before forming the extrudate) it is theorized that the low catalytic activity was caused by the nonuniform distribution of Pd atoms in the extrudates. In other words, it is believed that there is a diffusion problem for Pd ions from outside to interior of extrudate. It is also highly possible that most Pd ions anchored on the nanotubes were located near the external surface of extrudate, with only a small portion of Pd in the interior of extrudate. This would result in large Pd particles in the external area and small Pd particles in the interior area of extrudate. Therefore, the apparent Pd dispersion decreased. When the extrudates were crushed, some granules have high Pd loading with large Pd particles, while others have low Pd loading with small Pd particles, and yet others granules might not have any Pd particles. Low catalytic activity is expected when the granules with large or no Pd particles dominate the supported catalyst mixture.

Example 3

Pd was loaded onto $HNO_3$ oxidized CC nanotubes (i.e., CC aggregates which have been oxidized with $HNO_3$) via ion exchange at room temperature in $Pd(NH_3)_4(NO_3)_2$ solution. The solution was evaporated and nanotubes with 0.5 wt % Pd supported thereon remained. The Pd/nanotubes were ground to powder. 0.6 g of $H_2O$ were added to 0.2 g of the Pd/nanotube powders. Half of the wet powder mixture was put into a ½" pellet die. The die was pressured under 1,500 psi at room temperature for about 30 seconds. The thickness of the pellet is about 1.7 mm. The pellet was dried under vacuum at 100° C. for 3 hrs. The apparent Pd dispersions were measured by CO chemisorption for the Pd/nanotube powders (i.e., prior to die press) and the pellets (i.e., die pressed). The results are displayed in Table 5.

TABLE 5

| Catalyst | Loading (wt %) | Form | Pd dispersion (%) | Pd particle size (nm) |
|---|---|---|---|---|
| Pd | 0.5 | Powder | 50.0 | 2.2 |
| Pd | 0.5 | Pellet | 58.5 | 1.9 |

Table 5 revealed that the Pd/nanotube pellet has higher apparent Pd dispersion than the Pd/nanotube powder.

Figure 3:
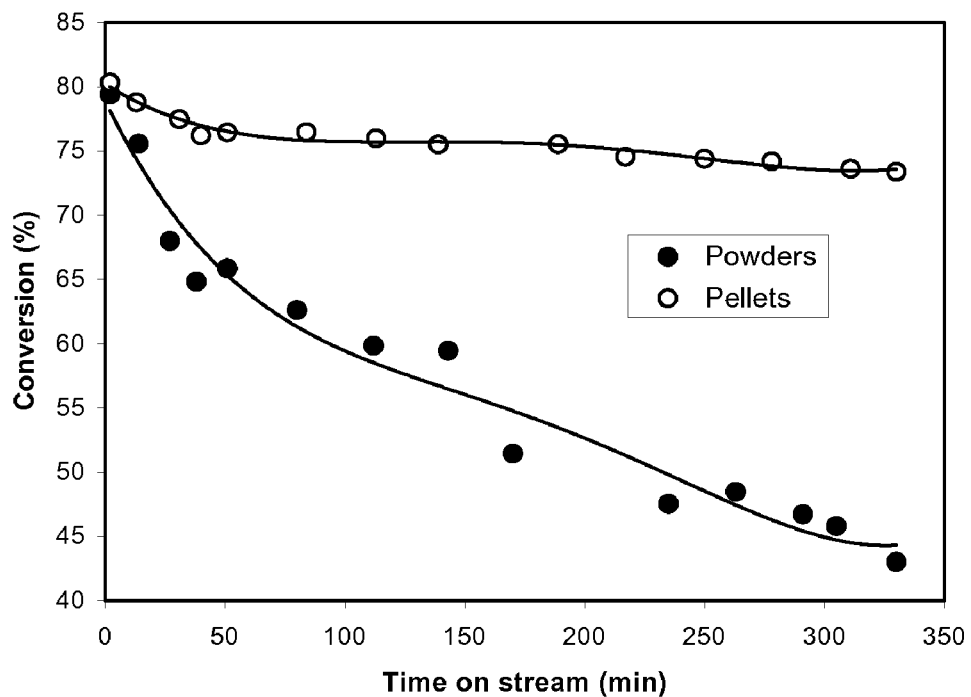
FIG. 3 displays the results of the hydrogenation of cyclohexene using 0.5 wt % supported Pd catalysts in powder and pellet form as prepared in accordance with Example 3.
Figure 4:
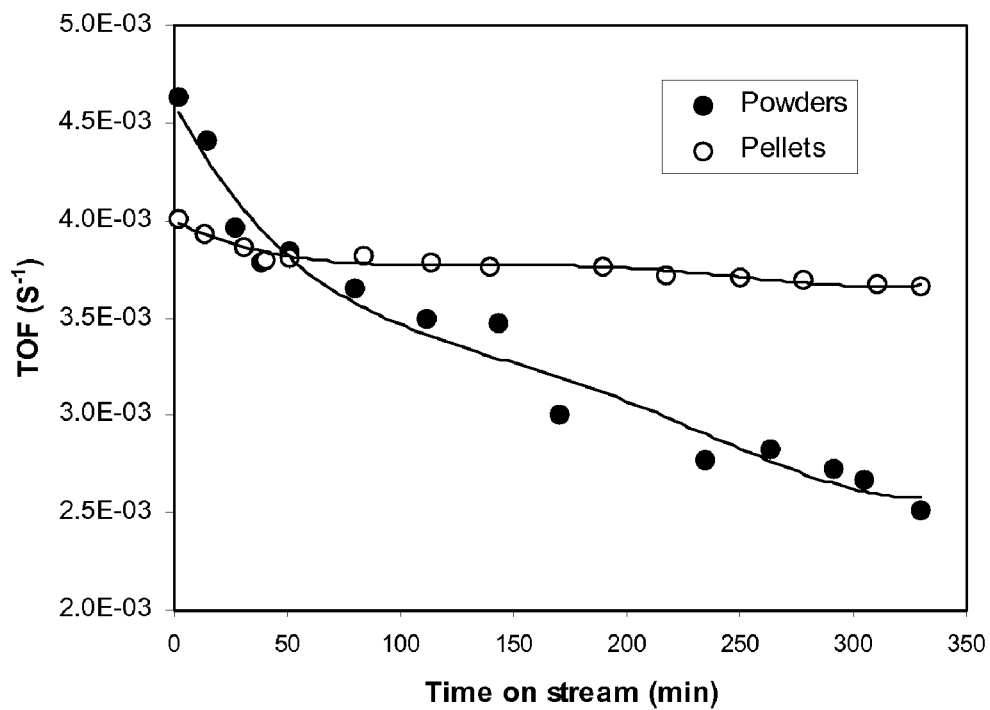
FIG. 4 displays the results of the hydrogenation of cyclohexene using 0.5 wt % supported Pd catalysts in powder and pellet for as prepared in accordance with Example 3.

Furthermore, the catalytic activity of these supported catalysts were examined for cyclohexene hydrogenation using the same conditions as Example 2 and the results are shown in FIGS. 3 and 4. FIGS. 3 and 4 revealed that Pd/nanotube pellets had both higher overall catalytic activity and more surprisingly, higher stability for cyclohexene hydrogenation than the Pd/nanotube powders. The granule size for both catalysts was between 20 and 40 mesh.

With respect to the high stability, the initial conversion of cyclohexene was approximately the same for both catalysts. However, as shown in FIGS. 3 and 4, the conversion of cyclohexene in the presence of the Pd/nanotube powders decreased measurably over time and did not reach a steady state condition within the 350 minutes allotted for the experiment. On the other hand, the conversion of cyclohexene in the presence of Pd/nanotube pellets decreased slightly in comparison, and reached steady state conditions within the allotted time of the experiment. These results show that a carbon nanotube structure formed from nanotubes on which Pd has been predeposited not only retains its dispersion, but that this is reflected in reaction performance.

Example 4

The process for preparing Pd/nanotube extrudate supported catalysts from Example 2 was repeated. However, the Pd/nanotube extrudates were ground in two stages. After the initial ground, smaller particles of extrudate were ignored, and the larger particles of the extrudates were selectively collected, ground again and sieved to obtain particles between 20 and 40 mesh. It was believed that the larger extrudate particles originated from the exterior of the extrudate since the exterior part has higher density and strength than the interior of the extrudate. The exterior part of the extrudate would also contain more Pd atoms than the interior part of the extrudate due to the ion exchange method used for loading the Pd onto the already formed extrudate.

Figure 5:
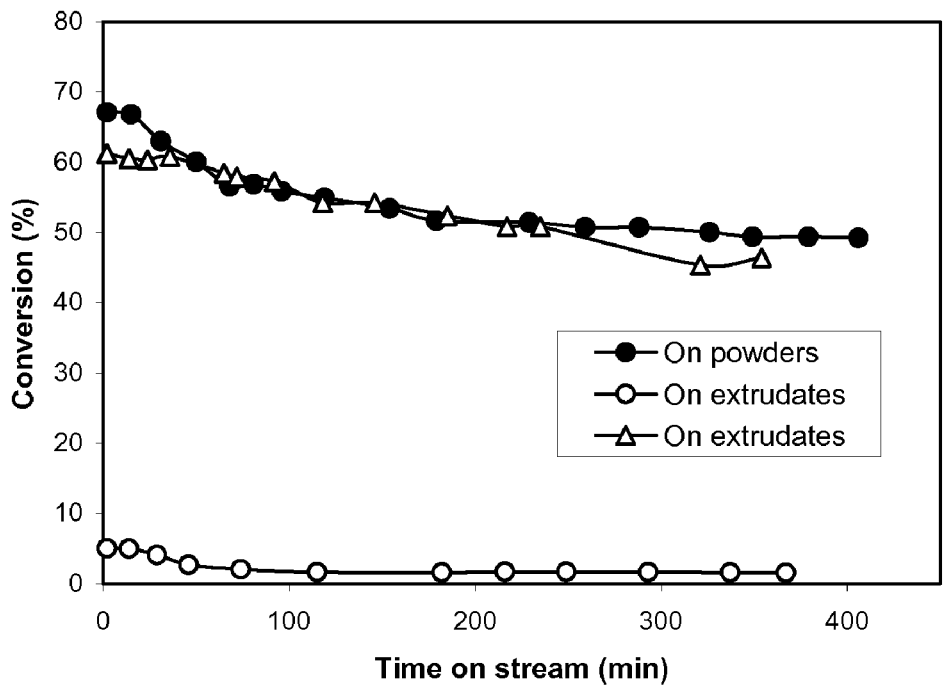
FIG. 5 displays the results of the hydrogenation of cyclohexene using 0.5 wt % supported Pd catalysts as prepared in accordance with Example 4.

The catalytic activity of this re-sampled Pd/extrudate catalyst support was then examined for cyclohexene hydrogenation under the same conditions as Example 2. The new results are indicated with open triangles in FIG. 5, which also includes the results from Example 3 for comparison.

The re-sampled Pd/extrudate catalysts of this example showed comparable catalytic activity to the Pd/nanotube powders.

Example 5

Pd/nanotube powders and Pd/nanotube pellets were prepared following Example 2, except that 0.2 wt % Pd/nanotube catalyst samples were prepared instead of 0.5 wt % Pd/nanotube catalyst samples as in Example 3. The hydrogenation of cyclohexene on the particles crushed from the pellets was carried out and the results are displayed in FIG. 6.

Figure 6:
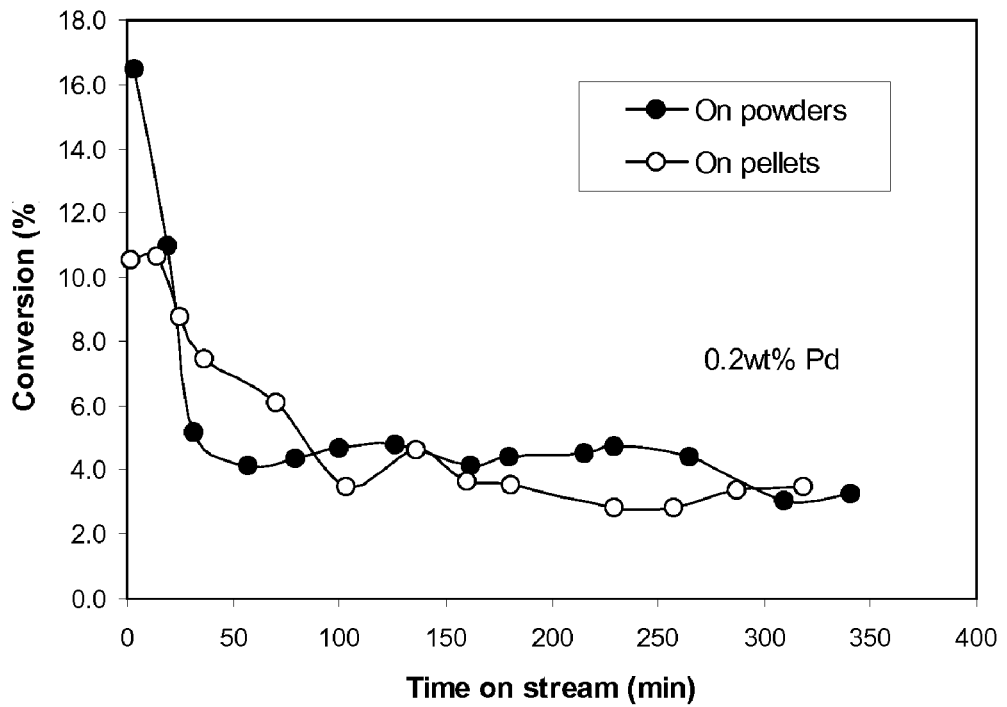
FIG. 6 displays the results of the hydrogenation of cyclohexene using 0.2 wt % supported Pd catalysts as prepared in accordance with Example 5.
Figure 7:
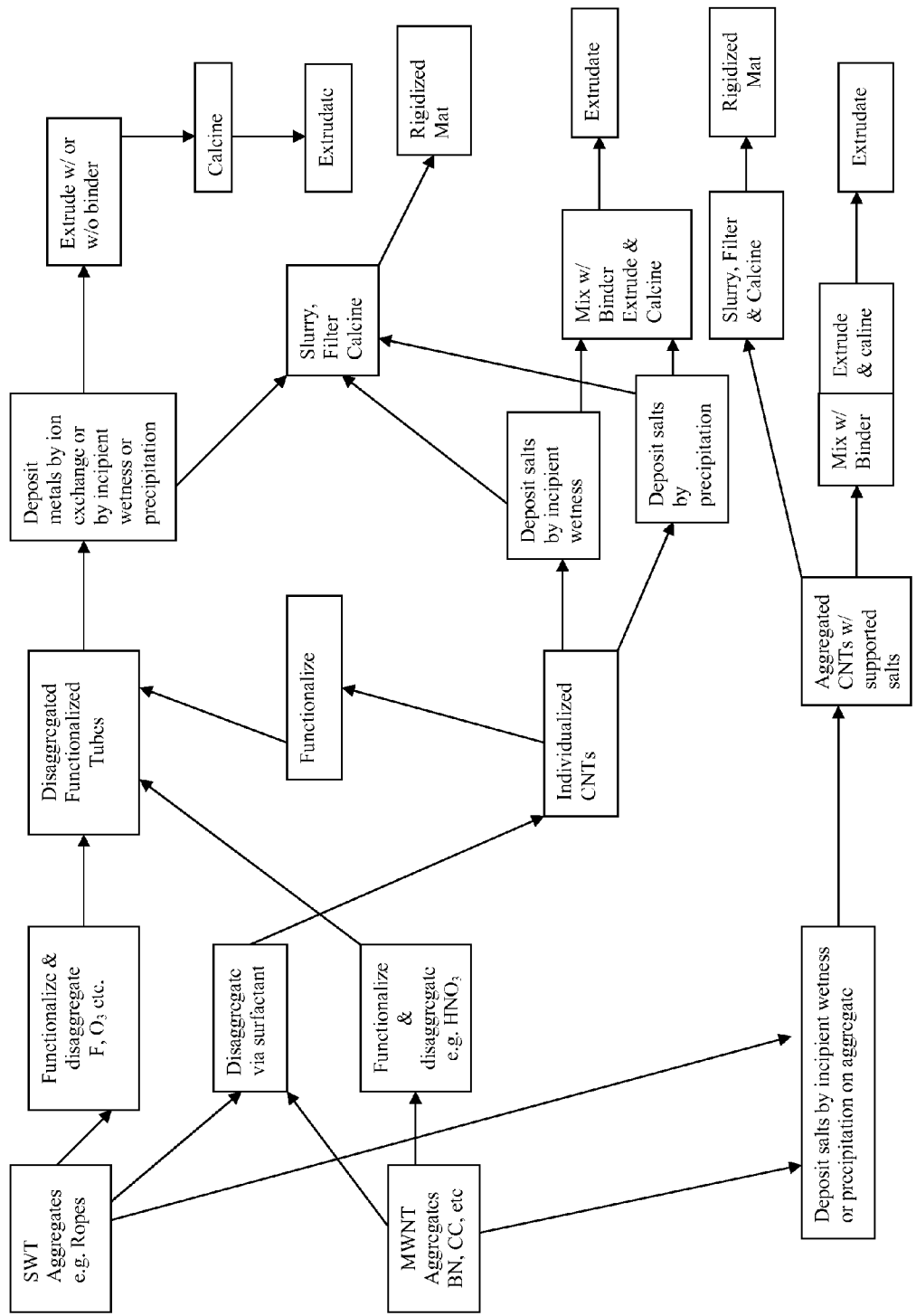
FIG. 7 is a flow chart illustrating the various embodiments of the present invention.

FIG. 6 revealed, unlike the results for Example 3, that the catalytic activities of the 0.2 wt % Pd/nanotube powders and pellets were comparable.

Example 6

CC nanotubes were extruded with PAM-3K polymer binder. The extrudates were then calcined in Ar at 600° C. for 2 hr and functionalized with 35% $HNO_3$ at 80° C. for 2 hr. The extrudates were not ground prior to loading Pd.

Three loadings of Pd/nanotube extrudate catalysts were prepared. The supported catalyst with 0.5 wt % Pd was prepared with $Pd(NH_3)_4Cl_2$ solution by ion exchange at room temperature for 24 hrs.

The supported catalysts with 1.5 wt % and 3 wt % of Pd were prepared by incipient wetness impregnation with $PdCl_2$/HCl solution at room temperature.

Apparent Pd dispersions were measured by CO chemisorption at room temperature and the results are displayed in Table 6. The apparent Pd dispersion of the 3.0 wt % Pd/nanotube extrudate catalyst was further compared to other Pd/nanotube powder catalysts oxidized under different conditions as reported in Table 7. The samples were reduced at 300° C. for 2 hr prior to the chemisorption.

TABLE 6

Apparent Pd dispersion for Pd catalysts supported on functionalized CC nanotube extrudates

| Catalyst | Nominal Loading (wt %) | Pd dispersion (%) | Pd Particle size (nm) |
|---|---|---|---|
| A | 0.5 | 17.0 | 6.6 |
| B | 1.5 | 30.1 | 3.7 |
| C | 3.0 | 35.1 | 3.2 |

TABLE 7

Comparison between the catalysts supported on different nanotube supports

| Catalyst | Support | Oxidation conditions | Nominal Loading (wt %) | Pd dispersion (%) | Pd Particle size (nm) |
|---|---|---|---|---|---|
| C | Extrudate | 35% $HNO_3$/ 80° C./2 hr | 3.0 | 35.1 | 3.2 |
| D | Powder | 35% $HNO_3$/ 80° C./2 hr | 3.0 | 30.9 | 3.6 |
| E | Powder | 60% $HNO_3$/ 116° C./4 hr | 3.0 | 44.4 | 2.5 |

Example 7

Pd/nanotube extrudates were prepared using the process of Example 6, except that the extrudates were oxidized with ozone instead of $HNO_3$. Without breaking into small pieces, the whole extrudates were loaded with Pd by ion exchange in $Pd(NH_3)_4(NO_3)_2/H_2O$ solution at room temperature. The nominal loading of Pd was about 0.5 wt %. The apparent Pd dispersion measured by CO chemisorption at room temperature was 37.4%, which was lower than the 47.9% for the Pd catalyst supported on ozone-oxidized CC nanotube powders.

Example 8

Extrudates prepared from CC nanotubes using the same method as Example 2 were oxidized with ozone at room temperature. Prior to loading Pd, 0.5 g of ozone treated CC nanotube extrudates were hydrated with 1.0 ml of DI water and dried at 100° C. under vacuum over night. 3.0 ml of $PdAc_2$/acetone solution containing 2.5 mg of Pd was mixed with the extrudates, and the excess acetone was vaporized at room temperature. Some orange color solids were observed on the wall of crucible. About 1-2 ml of acetone was added in order to dissolve the solids. When the acetone was vaporized, the amount of solids remaining appear to decrease. Acetone was added and vaporized 3 times until the solids almost disappeared.

The Pd/nanotube extrudates were the dried at 60° C. under vacuum for 1 hr, then at 100° C. for another hour, and then kept in the oven till cooled to room temperature. The apparent Pd dispersion, as measured by CO chemisorption at room temperature, was 39.1%, which is lower than 57.8% for the Pd/nanotube powders (prepared with ozone as the oxidizing agent) loaded using the same procedure.

Example 9

The effects of heating and evacuation on Pd dispersion and extrudate strength were examined. Extrudates were made by extrusion of $HNO_3$ oxidized CC nanotube powders. They were calcined in Ar at 240° C. for 2 hrs. The acid titer exhibited upon titration was about 0.668 meq/g. 0.5 g of $HNO_3$ oxidized CC nanotube powders and extrudates was loaded in a flask which was well sealed and was connected to a vacuum system. The flask was evacuated to 100 mTorr, and was heated at 120° C. and 100 mTorr for 30 min. When the flask was cooled to room temperature, 5.0 ml (3.0 ml for extrudates) of $PdAc_2$/acetone solution containing 2.5 mg of Pd was injected into the flask. A number of extrudates fell apart when solution was added—thus, confirming that heating and evacuation do not necessarily improve extrudate strength. The excess acetone was removed by evaporation at room temperature. The catalyst was dried at 100° C. under vacuum for 1 hr, then at 40° C. overnight.

For comparison, the comparable catalysts (i.e., samples 3 and 5) were prepared without the application of heating and evacuation. The apparent Pd dispersions were measured using CO chemisorption at room temperature and are reported in Table 8:

TABLE 8

Apparent Pd dispersion for Pd catalysts supported on concentrated $HNO_3$ oxidized CC nanotube powders or extrudates

| Catalyst | Support | Heating & evacuation | Nominal Loading (wt %) | Pd dispersion (%) | Pd Particle size (nm) |
|---|---|---|---|---|---|
| 3 | Extrudate | No | 0.5 | 33.4 | 3.4 |
| 4 | Extrudate | Yes | 0.5 | 30.4 | 3.7 |
| 5 | Powder | No | 0.5 | 56.7 | 2.0 |
| 6 | Powder | Yes | 0.5 | 57.8 | 1.9 |

Table 8 revealed that treatment with heating and evacuation does not necessarily improve Pd dispersion (i.e., compare samples 3 vs. 4; samples 5 vs. 6).

Example 10

Competitive ion exchange is normally used in introducing and homogeneously distributing small amounts of precious metal on a support with a large surface area. It is more effective when used for loading metal catalysts onto cylindrical pellets than onto powders because it helps to improve mass transfer. In this example, $NH_4^+$ was chosen as the competitive ion for $Pd(NH_3)_4^+$ in the preparation of 0.5 wt % of Pd catalyst supported on extrudates.

0.5 g of ozone-oxidized plain CC nanotubes were extruded to form extrudates. The extrudates were added to a flask with 25 ml of $Pd(NH_3)_4(NO_3)_2$ and $NH_4Ac$ water solution that contains 2.5 mg of Pd and 61.7 mg of $NH_4Ac$. The mixture system was stirred with mechanic stirrer at room temperature for 24 hr. After filtered and washed thoroughly with DI water, the catalyst was dried under vacuum at 100° C. for 2 hr. Apparent Pd dispersion was measured using CO chemisorption at room temperature and the results are reported in Table 9:

TABLE 9

Apparent Pd dispersion for Pd catalysts supported on CC nanotube extrudates

| Catalyst | Oxidation | Ions | Nominal Loading (wt %) | Pd dispersion (%) | Particle size (nm) |
|---|---|---|---|---|---|
| 7 | 35% HNO$_3$ | Pd(NH$_3$)$_4^+$ | 0.5 | 17.0 | 6.6 |
| 8 | Ozone | Pd(NH$_3$)$_4^+$ | 0.5 | 37.4 | 3.0 |
| 9 | Ozone | Pd(NH$_3$)$_4^+$ & NH$_4^+$ | 0.5 | 50.3 | 2.2 |
| 10* | Ozone | Pd(NH$_3$)$_4^+$ | 0.5 | 47.9 | 2.3 |

*Powders

Example 11

Supported catalyst 11 was prepared by impregnation with 5.0 ml PdAc$_2$/acetone solution at room temperature. Prior to impregnation, the ozone-oxidized CC nanotube powders were hydrated with water and were dried at 100° C. in a vacuum oven for 3 hrs.

Supported catalyst 12 was prepared by following the same procedure as supported catalyst 11 except for two differences: 1) nanotubes were not pre-hydrated; 2) PdAc$_2$ was dissolved in methanol instead of acetone.

Supported catalyst 13 was prepared by following the same procedure for making supported catalyst 11, except for two differences: 1) nanotubes were not pre-hydrated; 2) PdAc$_2$ was dissolved in acetone/H$_2$O mixture. The mixture contains 4 ml of PdAc$_2$/acetone solution and 1 ml of DI water.

The apparent Pd dispersion was measured by CO chemisorption at room temperature and the results are displayed in Table 10:

TABLE 10

Apparent Pd dispersion for Pd catalysts supported on ozone-oxidized CC nanotube powders

| Catalyst | Solvent | Nominal Loading (wt %) | Pd dispersion (%) | Particle size (nm) |
|---|---|---|---|---|
| 11* | Acetone | 0.5 | 57.8 | 1.9 |
| 12 | Methanol | 0.5 | 26.0 | 4.3 |
| 13 | Acetone/H$_2$O | 0.5 | 37.6 | 3.0 |

*pre-hydrated

Table 10 revealed that hydration of ozone-oxidized nanotubes prior to loading Pd can increase Pd dispersion when using acetone as solvent.

Example 12

10 grams of CC-type carbon nanotubes were placed in a 200 cc round bottom flask and 100 ml of 63% nitric acid was added and the temperature was raised to reflux condition for 2 hours. The product was then cooled down, filtered, and thoroughly washed with deionized water and dried at 80° C. Ammonium heptamolybdate with designated loading was then added to the oxidized carbon nanotubes by incipient wetness impregnation. Then the solid content in the metal loaded carbon nanotubes was measured and subsequently adjusted to 30-40% either by removing or adding extra solvent before extrusion was performed. The resulting extrudates were then dried and calcined in air at 250-300° C. Sulfurization of supported molybdenum oxides was carried out in a hydrogen/thiophene mixture with (10% thiophene in H$_2$) at 400 C to make Mo sulphide supported on carbon nanotube structures. The said catalyst was tested to be capable of catalyzing hydrodesulphurization of thiopene.

Example 13

A solution of CrCl$_3$.H$_2$O (3.15 g) in de-ionized water (50 mL) is prepared in a round-bottomed flask. 25.0 grams of oxidized carbon nanotubes (CC-type) are then added into the above solution and the slurry is stirred on a rotary evaporator at room temperature at ambient pressure for 2 hours. The water is then removed under vacuum and the solid content in the wet cake is controlled to be between 25-40% before extrusion. The extrudates is further dried at 130 C in nitrogen for 20 hours. The recovered catalyst is weighed 26.65 g and contained about 7.5 weight percent CrCl$_3$. The reaction, florination of CH$_2$Cl$_2$, is investigated in an nickel alloy reactor. At 275 C and the ratio of HF to CH$_2$Cl$_2$ of 4, a 50% selectivity of CH$_2$F$_2$ can be reached after 1 hour of reaction.

Example 14

CC-type of multiwalled carbon nanotubes are first oxidized by 63% nitric acid in a round bottom flask under reflux condition for 4 hours. After filtration and thorough wash with deionized water, the filter cake is further dispersed in water under sonication. The solid content of this nanotubes suspension is kept under 0.05 wt %.

Single walled nanotubes made from a method described in U.S. Pat. No. 6,827,919 is first oxidized in nitric acid under the similar fashion as described previously. The resulting nanotubes are free of metal catalysts, and in the form of smaller and shorter bundles as compared to the as-made material. After filtration and thorough washed with deionized water and acetone sequentially, the product is dried carefully under vacuum at room temperature. The dried single-walled nanotubes are further treated with ozone using a method disclosed in a U.S. Provisional Application No. 60/621,132, filed Oct. 22, 2004, where functional groups such as carboxyls, hydroxyls, carbonyls, and lactones are more effectively produced on the surface of nanotubes. An 8-hour reflux with K$_2$PtCl$_4$ in dilute ethylene glycol (3:2 by volume of ethylene glycol:DI H$_2$O) at 1200-130° C. then deposits Pt particles onto the single-walled nanotubes processed previously. Approximately 1.5 mg of K$_2$PtCl$_4$ and 20 ml of diluted ethylene glycol are added per 10 mg of single-walled nanotubes. The product (Pt-loaded SWNT bundles) is cooled, centrifuged, washed with DI water made slightly acidic with a few drops of HCl (a nonoxidizing acid to destabilize the suspension). Typical metal loading of the final material is 10 wt % Pt. Deionized water is then added to Pt-loaded single-walled nanotubes to form a uniform suspension and mixed with multiwalled nanotubes suspension made previously under sonication. Finally, the resulting suspension is concentrated using a rotary evaporator, filtered, dried carefully to achieve a solid content of 20-40% and the extruded to form ⅛ inch cylindrical exudates. Finally, these exudates are calcinated in argon at 500° C. to form a rigid porous structure via cross-linking. The product is composed of small bundles of single-walled nanotubes loaded with 102 nm Pt particles locked inside a rigid porous structured multiwalled nanotubes.

The terms and expressions which have been employed are used as terms of description and not of limitations, and there is no intention in the use of such terms or expressions of excluding any equivalents of the features shown and described as portions thereof, it being recognized that various modifications are possible within the scope of the invention.

Thus, while there had been described what are presently believed to be the preferred embodiments of the present invention, those skilled in the art will appreciate that other and further modifications can be made without departing from the true scope of the invention, and it is intended to include all such modifications and changes as come within the scope of the claims.

We claim:

1. A method for preparing a supported catalyst comprising:
   de-aggregating aggregates of multiwalled carbon nanotubes to provide de-aggregated multiwalled carbon nanotubes;
   loading metal catalysts or metal catalyst precursors onto the de-aggregated multiwalled carbon nanotubes to form metal-loaded de-aggregated multiwalled carbon nanotubes; and
   forming a carbon nanotube structure from the metal-loaded de-aggregated multiwalled carbon nanotubes.

2. The method of claim 1, wherein the metal catalysts or metal catalyst precursors are selected from the group consisting of ruthenium, osmium, rhodium, iridium, palladium, platinum, silver, gold, and mixtures thereof.

3. The method of claim 1, wherein the metal catalysts or metal catalyst precursors comprise palladium.

4. The method of claim 1, wherein the metal catalysts or metal catalyst precursors are selected from the group consisting of oxides, halides, carbides, nitrides, phosphides and sulfides of Ti, V, Cr, Mn, Fe, Co, Ni, Cu, Zn, Y, Zr, Nb, Mo, La, Ce, W, and combinations thereof.

5. The method of claim 1, further comprising:
   functionalizing the de-aggregated multiwalled carbon nanotubes with a functionalizing agent to form functionalized de-aggregated multiwalled carbon nanotubes prior to loading metal catalysts or metal catalyst precursors onto the functionalized de-aggregated multiwalled carbon nanotubes to form metal-loaded de-aggregated multiwalled carbon nanotubes.

6. The method of claim 5, wherein the functionalizing agent comprises an oxidizing agent selected from the group consisting of potassium chlorate, sulfuric acid, $HNO_3$, persulfate, $H_2O_2$, $CO_2$, $O_2$, steam, $N_2O$, $NO$, $NO_2$, $O_3$, and $ClO_2$.

7. The method of claim 1, wherein the supported catalyst has essentially no loss in metal catalyst dispersion.

8. A method for preparing a supported catalyst comprising:
   de-aggregating aggregates of single-walled carbon nanotubes to provide de-aggregated single-walled carbon nanotubes;
   loading metal catalysts or metal catalyst precursors onto the de-aggregated single-walled carbon nanotubes to form metal-loaded de-aggregated single-walled carbon nanotubes; and
   forming a carbon nanotube structure from the metal-loaded de-aggregated single-walled carbon nanotubes.

9. The method of claim 8, wherein the metal catalysts or metal catalyst precursors are selected from the group consisting of ruthenium, osmium, rhodium, iridium, palladium, platinum, silver, gold, and mixtures thereof.

10. The method of claim 8, wherein the metal catalysts or metal catalyst precursors comprise palladium.

11. The method of claim 8, wherein the metal catalysts or metal catalyst precursors are selected from the group consisting of oxides, halides, carbides, nitrides, phosphides and sulfides of Ti, V, Cr, Mn, Fe, Co, Ni, Cu, Zn, Y, Zr, Nb, Mo, La, Ce, W, and combinations thereof.

12. The method of claim 8, further comprising:
   functionalizing the de-aggregated single-walled carbon nanotubes with a functionalizing agent to form functionalized de-aggregated single-walled carbon nanotubes prior to loading metal catalysts or metal catalyst precursors onto the functionalized de-aggregated single-walled carbon nanotubes to form metal-loaded de-aggregated single-walled carbon nanotubes.

13. The method of claim 12, wherein the functionalizing agent comprises an oxidizing agent selected from the group consisting of potassium chlorate, sulfuric acid, $HNO_3$, persulfate, $H_2O_2$, $CO_2$, $O_2$, steam, $N_2O$, $NO$, $NO_2$, $O_3$, and $ClO_2$.

14. The method of claim 8, wherein the supported catalyst has essentially no loss in metal catalyst dispersion.

15. A method for preparing a supported catalyst comprising:
   de-aggregating aggregates of carbon nanotubes to provide de-aggregated carbon nanotubes;
   loading metal catalysts or metal catalyst precursors onto the de-aggregated carbon nanotubes to form metal-loaded de-aggregated carbon nanotubes; and
   forming a carbon nanotube structure from the metal-loaded de-aggregated carbon nanotubes;
   wherein the carbon nanotubes are a mixture of multiwalled and single-walled carbon nanotubes.

16. The method of claim 15, wherein the metal catalysts or metal catalyst precursors are selected from the group consisting of ruthenium, osmium, rhodium, iridium, palladium, platinum, silver, gold, and mixtures thereof.

17. The method of claim 15, wherein the metal catalysts or metal catalyst precursors comprise palladium.

18. The method of claim 15, wherein the metal catalysts or metal catalyst precursors are selected from the group consisting of oxides, halides, carbides, nitrides, phosphides and sulfides of Ti, V, Cr, Mn, Fe, Co, Ni, Cu, Zn, Y, Zr, Nb, Mo, La, Ce, W, and combinations thereof.

19. The method of claim 16, further comprising:
   functionalizing the de-aggregated carbon nanotubes with a functionalizing agent to form functionalized de-aggregated carbon nanotubes prior to loading metal catalysts or metal catalyst precursors onto the functionalized de-aggregated carbon nanotubes to form metal-loaded de-aggregated carbon nanotubes.

20. The method of claim 19, wherein the functionalizing agent comprises an oxidizing agent selected from the group consisting of potassium chlorate, sulfuric acid, $HNO_3$, persulfate, $H_2O_2$, $CO_2$, $O_2$, steam, $N_2O$, $NO$, $NO_2$, $O_3$, and $ClO_2$.

* * * * *

UNITED STATES PATENT AND TRADEMARK OFFICE
CERTIFICATE OF CORRECTION

| | | |
|---|---|---|
| PATENT NO. | : 7,968,489 B2 | Page 1 of 1 |
| APPLICATION NO. | : 11/841359 | |
| DATED | : June 28, 2011 | |
| INVENTOR(S) | : Ma et al. | |

It is certified that error appears in the above-identified patent and that said Letters Patent is hereby corrected as shown below:

Column 24, Line 44 (Claim 19, Line 1): change "claim 16," to -- claim 15, --

Signed and Sealed this
Sixteenth Day of August, 2011

David J. Kappos
*Director of the United States Patent and Trademark Office*